United States Patent
Clement et al.

(10) Patent No.: US 7,294,114 B1
(45) Date of Patent: Nov. 13, 2007

(54) FOOT ORTHOTIC FOR SAFE AMBULATION

(75) Inventors: Richard J. Clement, Sudbury, MA (US); Julian Cherubini, Boston, MA (US); Jesse Drake, Clinton, MA (US)

(73) Assignee: AliMed, Inc., Dedham, MA (US)

( * ) Notice: Subject to any disclaimer, the term of this patent is extended or adjusted under 35 U.S.C. 154(b) by 97 days.

(21) Appl. No.: 11/335,225

(22) Filed: Jan. 19, 2006

(51) Int. Cl.
*A61F 5/00* (2006.01)
*A43C 13/08* (2006.01)

(52) U.S. Cl. .............................. 602/23; 36/15; 602/27

(58) Field of Classification Search .................. 602/23, 602/27, 28; 36/15, 62, 64, 65, 66, 117.3, 36/117.4
See application file for complete search history.

(56) References Cited

U.S. PATENT DOCUMENTS

| | | | | |
|---|---|---|---|---|
| 246,984 A | * | 9/1881 | Smith | 602/27 |
| 2,499,516 A | * | 3/1950 | Marceau | 36/66 |
| 4,542,599 A | * | 9/1985 | Annovi | 36/117.4 |
| 4,570,363 A | * | 2/1986 | Annovi | 36/117.4 |
| 5,020,523 A | * | 6/1991 | Bodine | 602/27 |
| RE33,762 E | * | 12/1991 | Lonardo | 602/27 |
| 5,088,479 A | * | 2/1992 | Detoro | 602/27 |
| 5,151,081 A | * | 9/1992 | Williams | 602/27 |
| 5,154,695 A | * | 10/1992 | Farris et al. | 602/27 |
| 5,224,925 A | * | 7/1993 | Varn | 602/28 |
| 5,269,748 A | * | 12/1993 | Lonardo | 602/27 |
| 5,352,189 A | * | 10/1994 | Schumann et al. | 602/23 |
| 5,368,551 A | * | 11/1994 | Zuckerman | 602/23 |
| 5,372,576 A | * | 12/1994 | Hicks | 602/27 |
| 5,446,977 A | * | 9/1995 | Nagano et al. | 36/131 |
| 5,460,600 A | * | 10/1995 | Bieling | 602/27 |
| 5,486,157 A | * | 1/1996 | DiBenedetto | 602/27 |
| 5,569,173 A | * | 10/1996 | Varn | 602/27 |
| 5,593,383 A | * | 1/1997 | DeToro | 602/27 |
| 5,665,059 A | * | 9/1997 | Klearman et al. | 602/27 |
| 5,735,805 A | * | 4/1998 | Wasserman et al. | 602/10 |
| 5,944,679 A | * | 8/1999 | DeToro | 602/27 |
| 6,056,712 A | * | 5/2000 | Grim | 602/27 |
| 6,277,087 B1 | * | 8/2001 | Hess et al. | 602/27 |
| 6,350,246 B1 | * | 2/2002 | DeToro et al. | 602/27 |
| 6,432,073 B2 | * | 8/2002 | Pior et al. | 602/10 |
| 6,923,780 B2 | * | 8/2005 | Price et al. | 602/27 |
| 2003/0046829 A1 | * | 3/2003 | Baechtold | 36/15 |

* cited by examiner

*Primary Examiner*—Michael Peffley
(74) *Attorney, Agent, or Firm*—Wolf, Greenfield & Sacks, P.C.

(57) ABSTRACT

An improved foot orthotic is disclosed which includes an L-shaped boot and a sole plate which mat be mounted to the boot using a bracket disposed in a recessed arch portion of the boot. Typically, a projection extends from the sole plate into the bracket. The projection may extend into a slot and may have an enlarged head which nests in a recess in the bracket. The sole plate may be removed by withdrawing the projection from the bracket. Preferably, the bracket is recessed so that when the wearer of the orthotic walks, the bracket does not touch the walking surface. A toe plate may also be used in conjunction with the boot. The toe plate may be mounted to the bracket independently of the sole plate. In one embodiment, the toe plate includes two arms separated by a slot. The two arms embrace a portion of the bracket. Mating ribs and recesses on the bracket and toe plate arms retain the toe plate in the desired position.

9 Claims, 7 Drawing Sheets

FOOT ORTHOTIC FOR SAFE AMBULATION

BACKGROUND OF INVENTION

1. Field of Invention

This invention relates generally to a foot orthotic, and more particularly to an improved connection for a sole plate.

2. Discussion of Related Art

Foot orthotics having a splint with an L-shaped configuration are well known. Examples are described in U.S. Pat. Nos. 5,269,748; 5,735,805; and 6,277,087. Such foot orthotics are most commonly used with bedridden patients and serve two different purposes. Firstly, these devices protect the patient's heel from bed sores. Secondly, they correct for a condition known as "foot drop" in which the patient's foot assumes an obtuse angle with respect to the patient's leg.

These foot orthotics may provide for attachment of a sole plate to the bottom thereof to allow the patient to walk while still wearing the orthotic. These sole plates provide traction and protect the patient and the orthotic from contamination. These sole plates preferably are removable to prevent contamination of the bed of the patient when the patient returns thereto. Typically, a connector is provided on the bottom of the orthotic to allow attachment and removal of the sole plate.

At night or at other times when the patient must leave the bed, such as to visit the bathroom, there is often not sufficient time to attach the sole plate. Moreover, some patients have difficulty attaching the sole plate without assistance. Therefore, the patient will make the trip from the bed to the bathroom, or to some other location, without taking the time or having the ability to attach the sole plate. In some types of orthotics, such as that shown in U.S. Pat. No. 5,735,805, the sole plate is secured by an attachment screw which extends vertically downwardly from the orthotic in the vicinity of the arch. This screw typically remains attached at all times. The distal end of the screw typically has a rounded head that provides little traction. With this type of orthotic, when the patient steps out of the bed without having attached the sole plate, the screw projects sufficiently far from the orthotic to engage the floor surface while the patient is walking. As a result, the entire weight of the patient may be supported by a single screw with a rounded, smooth head in substantially the center of the foot. The result is a rather unstable condition in which the patient's foot and ankle may rock from side to side or front to back, or may pivot about this screw. Moreover, since the screw has little or no traction, there is a risk that the patient could lose traction on the floor and slip, particularly if the patient is in a hurry. Because of this highly unstable condition, the patient is at risk of falling down, or twisting his/her ankle or knee, all of which could result in serious injury to the patient. This problem is exacerbated by the fact that this situation may occur at night when the patient is sleepy, disoriented or cannot see well.

It is therefore desirable to provide an orthotic with a coupling for a sole plate which provides a stable walking condition for the patient when he or she walks without the sole plate.

Toe extenders or toe plates are often used in conjunction with orthotics to protect the patient's toes both while walking and while in bed. The toe extender keeps the sheets and covers at a distance from the exposed toe when in bed. When walking, the toe extender prevents the toe from being injured or becoming soiled as a result of contact with the walking surface. The toe extender also prevents any damage to the exposed toes resulting from accidentally kicking an object as the person walks or otherwise moves about.

It is also desirable to provide an improved attachment for a toe extender or toe plate that could be used, if desired, with a sole plate.

SUMMARY OF INVENTION

This invention relates generally to an improved foot orthotic, and more particularly to a foot orthotic which includes a sole plate, and a connector between a boot and the sole plate that is positioned and configured to provide a stable walking surface when the sole plate is not attached. This invention allows a person wearing the orthotic to walk without attaching the sole plate without fear of injury or falling down.

In one aspect, a foot orthotic is disclosed which comprises, in one embodiment, a boot, the boot having a toe portion having a forward end, a recessed arch portion and a heel, a sole plate removably mountable on the boot, the sole plate having a textured surface on a first side for engagement with a walking surface and an upstanding projection disposed on a second side opposite the first side, and a bracket disposed on the boot, the bracket having a slot for receiving the projection on the sole plate, the bracket having a lower wall spaced from the boot and structured to face the sole plate, the lower wall of the bracket being spaced from a line connecting the forward end of the toe portion of said boot and the heel of said boot on the side of the line facing the arch portion.

In another embodiment, the foot orthotic may include mating portions of a hook and loop fastener disposed on opposed, confronting surfaces of the boot and the sole plate. In another embodiment, the foot orthotic further includes a toe plate mountable on the bracket independently of the sole plate. In one embodiment, the toe plate comprises a toe pad for supporting toes and at least one arm insertable into the bracket at a location spaced from the sole plate for retention of the sole plate on the bracket. The toe plate may comprise two parallel arms forming a slot therebetween for embracing a portion of the bracket. In yet another embodiment, mating ribs and ridges may be disposed on opposed, interlocking surfaces of the bracket and the arms of the toe plate. In yet another embodiment, the projection may comprise an enlarged head disposed on an end thereof spaced from the sole plate, and the bracket may comprise a recess for nesting of the enlarged head. In yet another embodiment, the bracket may comprise a slot surrounded by upstanding walls, wherein the projection on the sole plate includes an enlarged head spaced from the second side of the sole plate, the enlarged head being structured to ride along the upstanding walls of the bracket as the projection passes through the slot of the bracket. In another further embodiment, the bracket is disposed in the recessed arch portion of the boot.

In yet another aspect, a combination is disclosed including a boot having a generally L-shaped configuration and a toe portion, a heel, a concave arch portion and a leg portion; a sole plate removably attached to the boot and extending generally from the heel to the toe portion of the boot, the sole plate having an upstanding projection disposed on an upper surface thereof facing the boot; and a bracket disposed in the concave arch portion of the boot, the bracket receiving an enlarged upper end of the projection. In another embodiment, this combination may also include a toe plate connected to the bracket independently of the sole plate.

BRIEF DESCRIPTION OF DRAWINGS

The objects, advantages and features of this invention will be more clearly appreciated from the following detailed description, when taken in conjunction with the accompanying drawings, in which.

DETAILED DESCRIPTION

This invention relates generally to a foot orthotic that has an improved coupling device for attachment of a sole plate. In particular, the attachment device is configured so as to be positioned, such as within the arch recess between the heel and toe portions of the orthotic, so that when the heel and toe portions touch the ground, the attachment device is spaced from the ground. There is no screw or post or the like extending from the splint in the absence of a sole plate. In this way, if a patient decides to take a walk without affixing the sole plate, the foot orthotic will still be stable and will not cause injury to the patient.

In one aspect of the invention, a foot orthotic includes a novel attachment device disposed on the bottom in the vicinity of the arch recess onto which the sole plate may be attached. In one embodiment, the sole plate is attached utilizing a projection with an enlarged head which rides along a slot having inwardly extending lips which support the enlarged head.

In another aspect of the invention, the same attachment device may also accommodate a toe plate. In one embodiment of this aspect, the toe plate includes at least one arm which may be inserted into the attachment device. An outwardly extending rim on the attachment device assists retaining the toe plate in position. In another embodiment, the toe plate may include a slot separated by two arms which embrace a portion of the attachment device. The arms may include recesses which engage correspondingly formed ribs on the outside surface of the attachment device. The toe plate may be used either with or without the sole plate. Similarly, the sole plate may be used with or without the toe plate.

Figure 1:
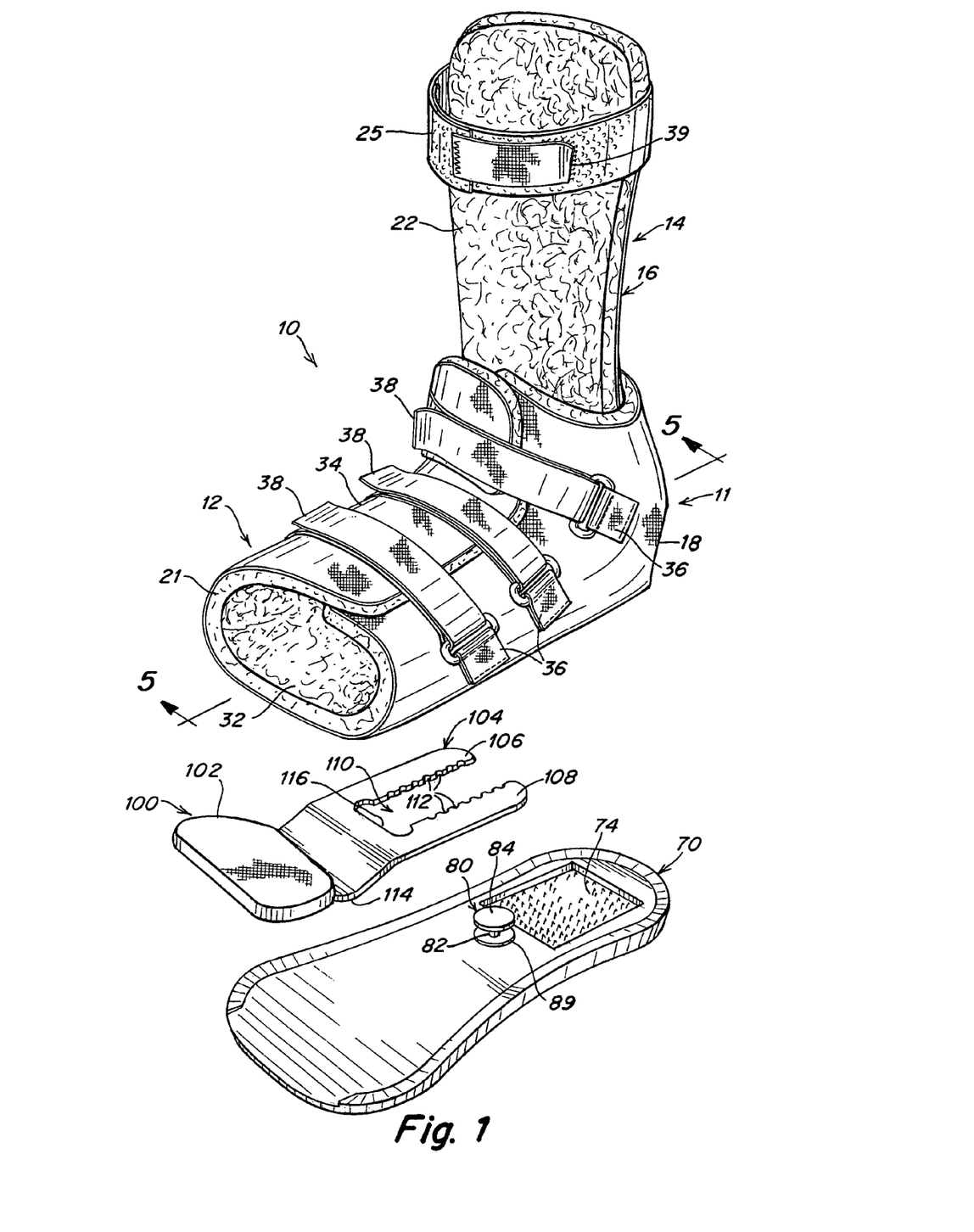
FIG. 1 is an exploded perspective view of the orthotic of this invention.
Figure 4:
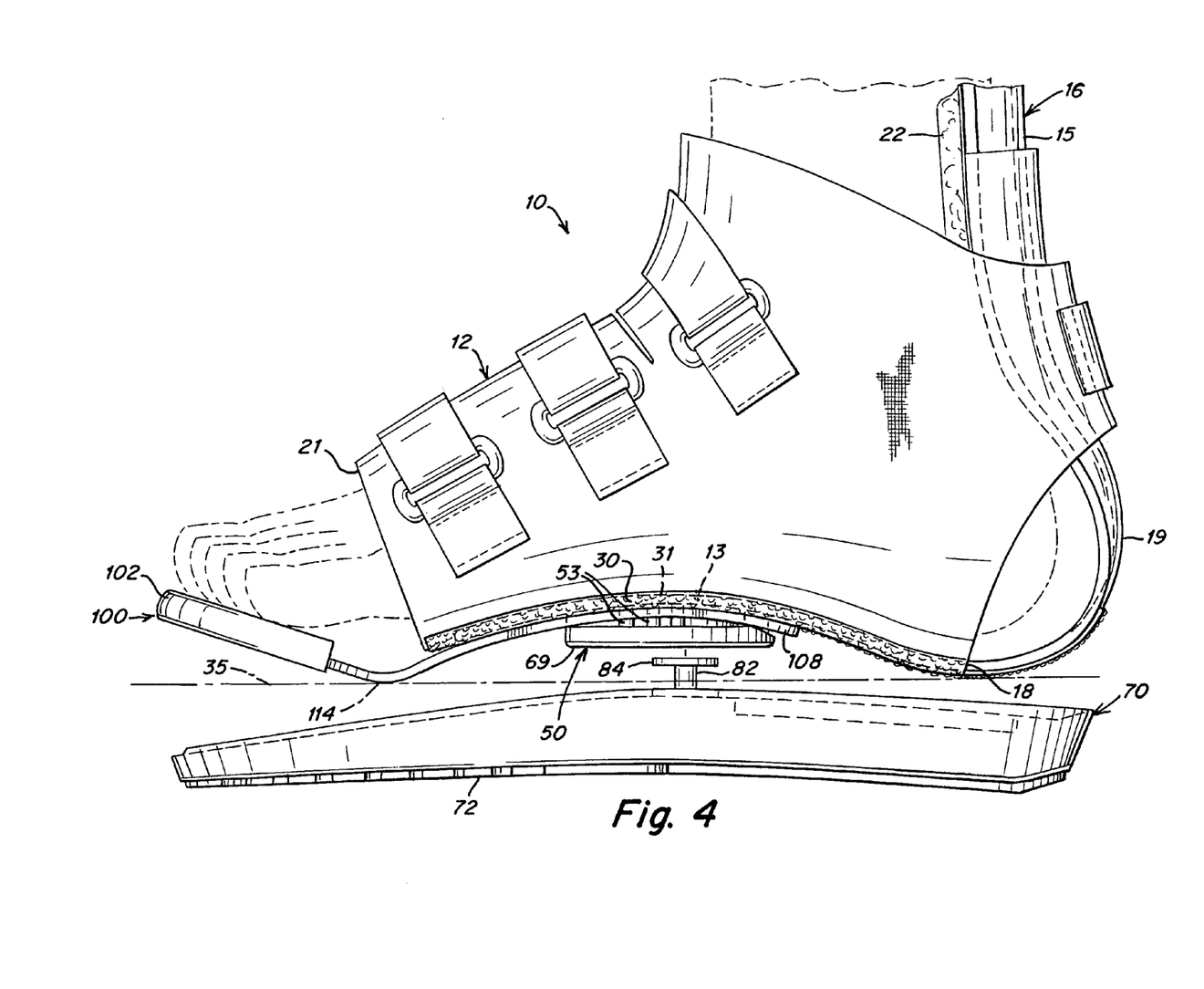
FIG. 4 is an exploded side view of the configuration shown in FIG. 3.
Figure 5:
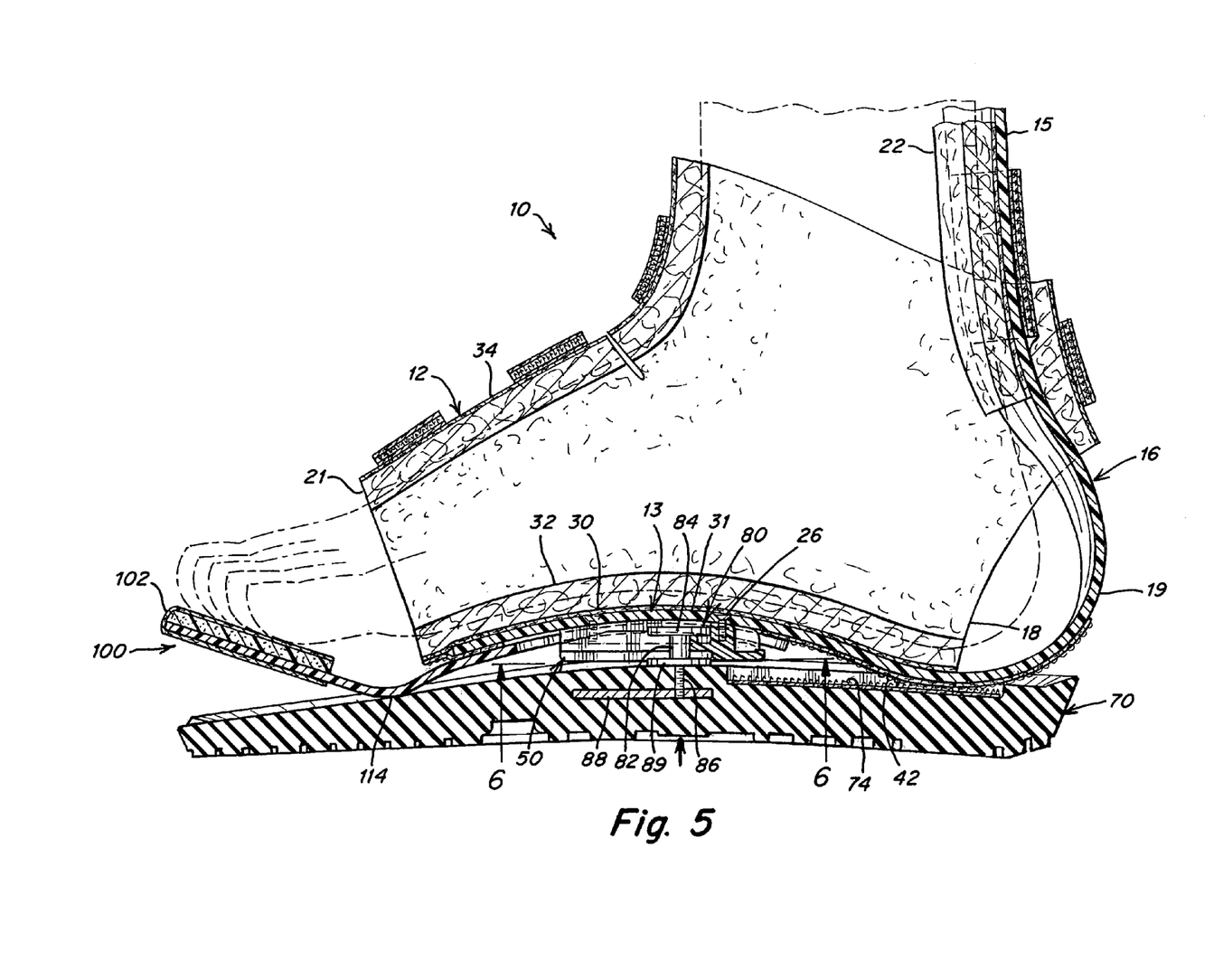
FIG. 5 is a cross-sectional side view of the fully assembled orthotic taken along the line 5-5 of FIG. 1.

With reference now to the drawings, and more particularly to FIGS. 1 and 4 thereof, the foot orthotic 10 of this invention will now be described. Orthotic 10 is L-shaped and includes a boot 11 having a foot portion 12, a leg portion 14 and a heel 18. Orthotic 10 also may include an L-shaped splint 16 that includes foot portion 13, heel 19 and leg portion 15, as shown in FIGS. 4 and 5. Boot 11 and splint 16 are conventional, except as noted hereinbelow, and need not be described in great detail.

The foot portion 13 of splint 16 is generally disposed at approximately right angles to the leg portion 15 of splint 16. The heel 19 of splint 16 typically is rounded to protect the heel and is spaced from the heel of the user, when worn. Splint 16 typically is substantially rigid, although some flexing at heel 18 may be permitted to help to maintain the foot in the desired angular relationship with respect to the leg. Splint 16 is typically formed of a plastic material such as an acrylic thermoplastic material. Leg portion 15 may extend, upwardly along the posterior region of the lower leg. Leg portion 15 may be contoured and channeled to comfortably receive the posterior region of the lower leg. Typically, although not necessarily, leg portion 15 is recessed just above the ankle bone and below the greater calf to act as a support for the leg and receive most of the weight concentration on the leg when standing. Padding 22 may be disposed on the leg portion 14 of boot 11 adjacent leg portion 15 to provide a cushion for the user. A strap 25 having a fastener 39, such as a hook and loop fastener (such as VELCRO®), may be used to attach leg portion 14 to the leg.

Foot portion 12 of boot 11 and foot portion 13 of splint 16 extend from respective heels 18 and 19 forwardly and both include respective arch portions 30 and 31 which are concave upwardly to accommodate the arch of a normal person. Foot portions 12 and 13 typically, although not necessarily, terminate at end 21 short of the patient's toes when worn, as shown in FIG. 4. Padding 32 typically is provided on the foot portion 12 adjacent foot portion 13 of splint 16 to protect a patient's foot. Foot portion 12 may be provided with a wraparound flap 34 to attach foot portion 12 to the foot. Flap 34 may be held in place with straps 36 which typically, although not necessarily, are held in place with hook and loop fasteners 38 (such as VELCRO®) as is well-known in the art. Hook and loop fasteners 38 may be replaced with buckles, snaps, laces or the like as desired. The particular configuration of straps 25 and 36 and fasteners 38 and 39 is conventional, and does not form any part of this invention.

In one aspect of the invention, a novel sole plate and attachment for a sole plate are disclosed. This aspect will be described with particular reference to FIGS. 1 and 3-8. Orthotic 10 includes an attachment bracket 50, sole plate 70 and a sole plate mounting projection 80. Sole plate 70 typically is formed of rubber, plastic or another like material which is durable, and may provide for traction. On the side of sole plate 70 structured to engage a walking surface 35, a textured surface 72 typically is provided which may include a tread. In one embodiment, as illustrated herein, sole plate 70 may be formed entirely of a rubber or another like material, into which a tread design is molded or carved. On the side of sole plate 70 intended to face foot portion 12, typically, but not necessarily, there is included a layer 74 of the hook or loop portion of a hook and loop fastener intended to mate with a layer 42 of the other portion of a hook and loop fastener disposed on foot portion 12 and/or heel 18. One example of a suitable hook and loop fastener is a VELCRO® fastener.

Figure 7:
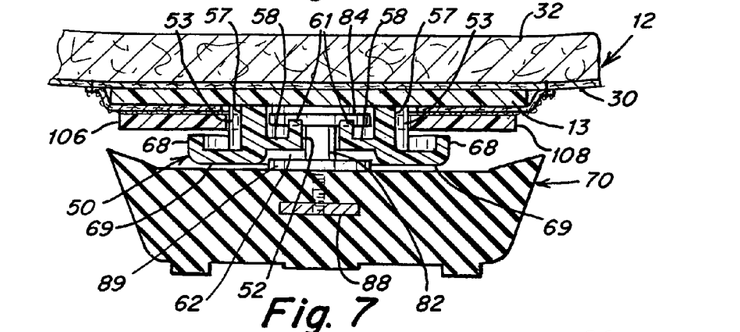
FIG. 7 is a cross-sectional end view of the attachment device taken along the line 7-7 of FIG. 6.

Also disposed on the upper surface of sole plate 70 and structured to face foot portion 12 is mounting projection 80. Projection 80 typically extends at a substantially right angle to the plane of the upper surface of sole plate 70. Mounting projection 80 typically includes a shaft 82 and an enlarged head 84 disposed on an end of shaft 82 spaced from sole plate 70. In the embodiment shown herein, head 84 has generally a circular, flat disc configuration. However, it is to be understood that head 84 may have other shapes, such as square or rectangular and is not limited to a circular configuration or to a flat, disc shape. The lower end 86 of projection 80 is mounted onto sole plate 70. In one embodiment, the lower end 86 of projection 80 is embedded into sole plate 70. In an alternative embodiment, as illustrated in FIGS. 5 and 7, projection 80 includes a lower flange 89 disposed on the upper surface of sole plate 70, and a plate 88 embedded in sole plate 70. Lower end 86 of projection 80 extends into sole plate 70 where it is mounted onto plate 88. Plate 88 may extend laterally along sole plate 70 to provide a stable and secure base for projection 80. However, it is to be understood, that the manner of affixation of projection 80 to sole plate 70 is not critical, and any means of affixation are acceptable, so long as projection 80 is securely attached to sole plate 70 and does not easily separate from sole plate 70 with use.

Attachment bracket 50 will now be described with particular reference to FIGS. 6-9. Attachment bracket 50 is mounted to the underside of foot portion 12. Attachment bracket 50 may be mounted in any commonly accepted fashion, such as by screws 26, rivets, adhesive or the like. Attachment bracket 50 is configured and positioned so that it does not touch a ground surface 35 when a patient walks without attaching sole plate 70. Preferably, bracket 50 is mounted in the recess provided by arch portion 30 of foot portion 12. As can be seen in FIG. 9, arch portion 30 has a curved, concave configuration which is indented relative to heel 18 and end 21. Typically, as shown in FIG. 9, when foot portion 12 rests on surface 35 without sole plate 70, so that heel 18 and end 21 are resting on surface 35, as shown by line 37 connecting heel 18 and end 21, lower wall 69 of attachment bracket 50 is spaced from surface 35, and does not contact it. This spacing between lower wall 69 and surface 35 becomes even greater when a toe plate 100 is utilized in conjunction with the structure, as shown in FIG. 4, as will be described. In this way, stable contact between foot portion 12 and surface 35 is provided.

Figure 3:
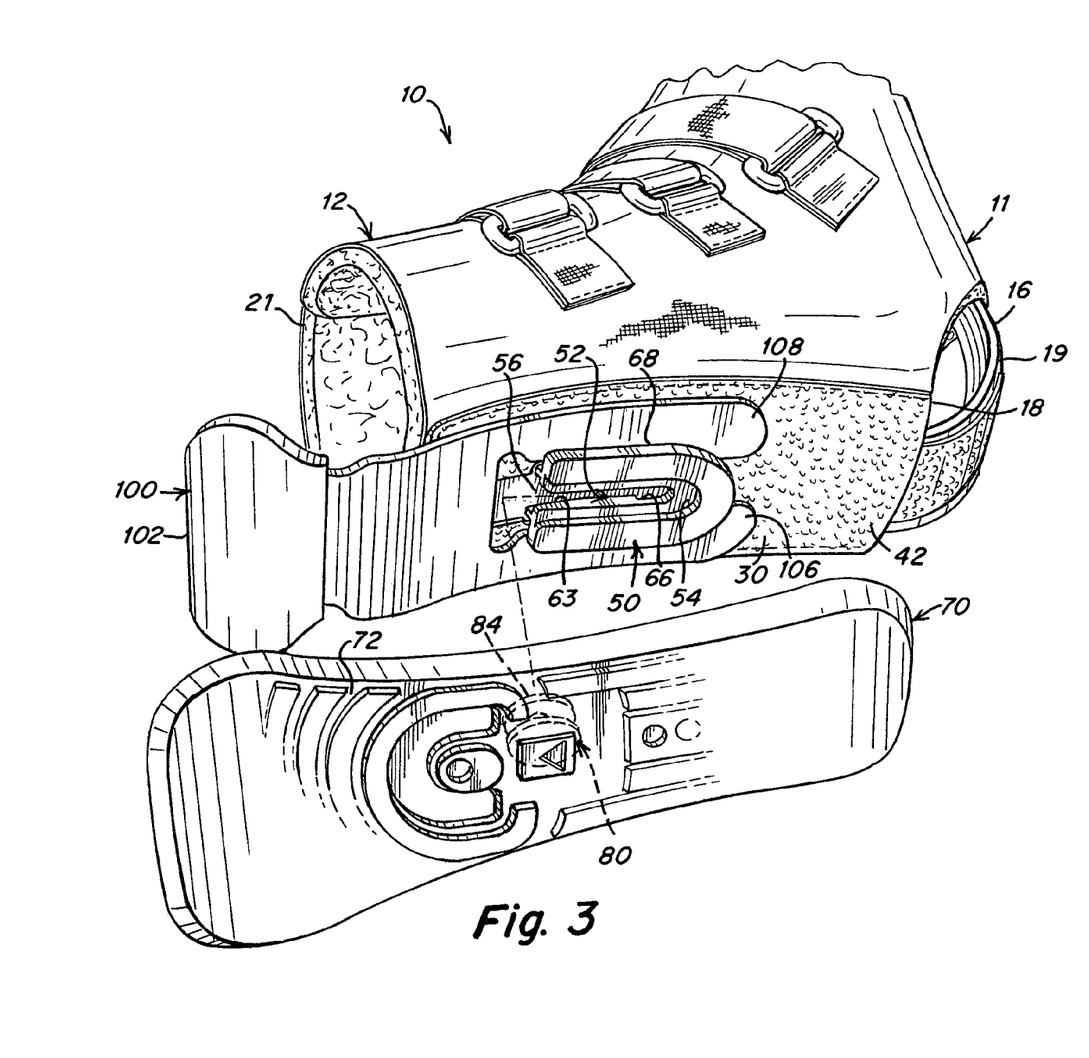
FIG. 3 is an exploded bottom perspective view of the sole plate and attachment device of this invention.

As shown in FIGS. 3 and 6-8B, in one embodiment, attachment bracket 50 includes a slot 52 which is typically closed at one end 54 and open at another end 56. As shown in FIG. 3, open end 56 preferably faces the end 21 of foot portion 12. However, it is to be understood that in another embodiment, open end 56 may face heel 18, or it may even face to one side or the other of foot portion 12. Slot 52 is sufficiently wide so that it can accommodate shaft 82 of mounting projection 80. As is more clearly shown in FIGS. 7, 8A and 8B, slot 52 includes lips 58 which extend inwardly into slot 52 from the sides of slot 52, and walls 61 which extend upwardly from lips 58 toward foot portion 12. When slid into position, head 84 resides on top of lips 58 and typically is captured between the upper edge of walls 61 of lips 58 and an upper surface 59 which may be the lower surface of foot portion 13 of splint 16. A ramp 63 may be disposed on the upper edge of walls 61 adjacent open end 56 of slot 52 to facilitate entry of head 84 into the space between walls 61 and surface 59. A recess 62 may be formed on the side of lips 58 facing away from foot portion 12 by recessing lips 58 with respect to wall 69 of bracket 50 to accommodate flange 89 of projection 80. In another embodiment, transverse shoulders 65 may be provided along the upper edge of walls 61 adjacent end 54 allowing head 84 to seat in a recess 66 between shoulders 65 and end wall 67 of bracket 50. Typically, but not necessarily, end wall 67 is shaped to conform to the shape of head 84. In the embodiment as shown, wall 67 is rounded with a radius of curvature similar to that of head 84.

Mounting and dismounting of sole plate 70 of this invention will now be described with particular reference to FIGS. 3 and 5-8B. Should a person desire to attach sole plate 70 to foot portion 12, projection 80 is aligned with open end 56 of slot 52, as shown in FIG. 3. Head 84 is pushed against upper surface 59 so that the lower surface of head 84, or the surface of head 84 facing sole plate 70, is disposed above the upper edge of ramp 63. A lateral force is then applied to sole plate 70 from open end 56 toward closed end 54. The lower surface of head 84 then rides over ramps 63, and along the upper edge of walls 61 until the lower surface of head 84 passes over shoulder 65 and into recess 66 formed between shoulder 65 and end wall 67, and between the upper surface of walls 61, and upper surface 59. Flange 86 typically resides within recess 62.

The mating portions of layer 74 of one component of a hook and loop fastener which is on sole plate 70 may be urged into engagement with layer 42 of the other component of a hook and loop fastener which is disposed on heel 18 and/or foot portion 12 (see FIG. 5). The use of this hook and loop fastener provides a secure bond between foot portion 12 and sole plate 70 to prevent rotation or other movement of sole plate 70 with respect to foot portion 12.

Figure 8A:
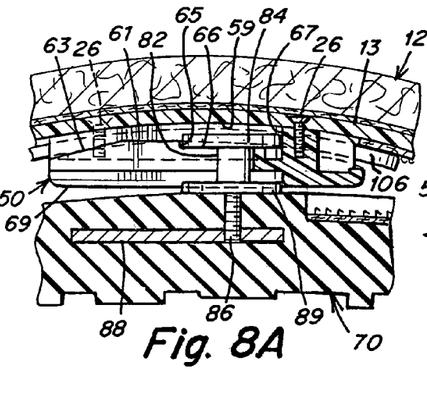
FIG. 8A is a cross-sectional side view taken along the line 8A-8A of FIG. 6.
Figure 8B:
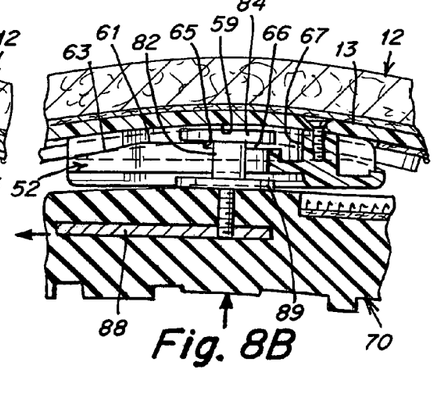
FIG. 8B is a cross-sectional side view similar to FIG. 8A but showing release of the sole plate.
Figure 9:
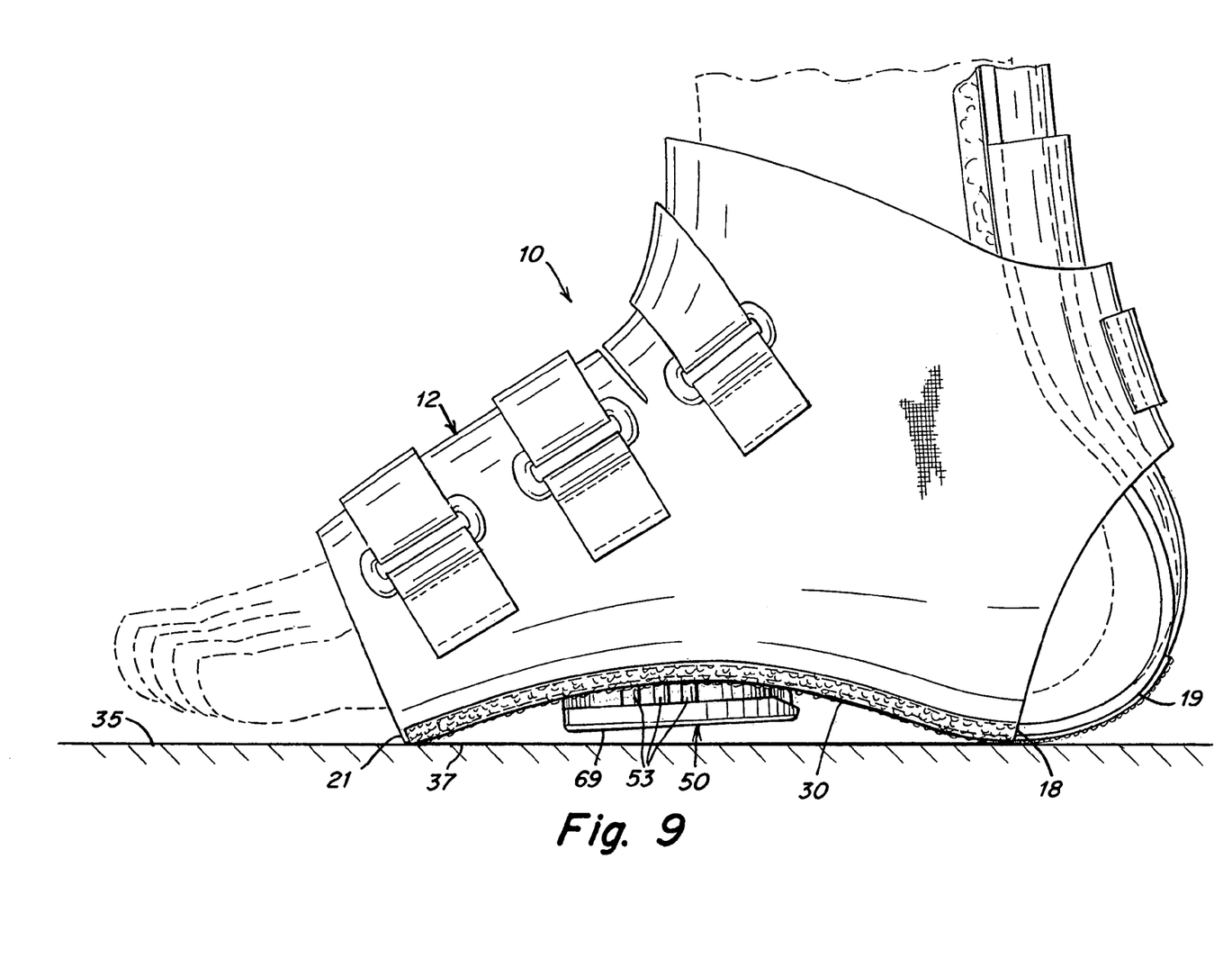
FIG. 9 is a side view of the orthotic of this invention resting on a walking surface without a toe plate and without a sole plate.

When it is desired to remove sole plate 70, an upward force toward foot portion 12 may be applied to the bottom of sole plate 70 to raise head 84 over shoulder 65, as shown in FIG. 8B. As shown in FIG. 3, the location of projection 80 may be indicated on the lower surface of sole plate 70, so that a user knows where to press upwardly on sole plate 70 to raise head 84 over shoulder 65. Layer 74 also is separated from layer 42, and a lateral force is applied to sole plate 72 toward open end 56, and away from closed end 54 of slot 52 (see FIG. 8B). Head 84 then rides along the upper surface of walls 61 and down ramp 63 at which point projection 80 is removed from bracket 50.

In another aspect of this invention, a toe plate 100 may be provided. For ease of illustration, FIGS. 1-8B all illustrate toe plate 100 as being attached at the same time that sole plate 70 is attached. However, it is to be understood that sole plate 70 may be used with or without toe plate 100 and that toe plate 100 may be used with or without sole plate 70. The invention is not intended to be limited in this respect. In one embodiment, toe plate 100 is mounted onto the same attachment bracket 50 onto which sole plate 70 is mounted. However, it is to be understood that toe plate 100 could be mounted onto another bracket or mounting device, and need not be attached to bracket 50.

Figure 2:
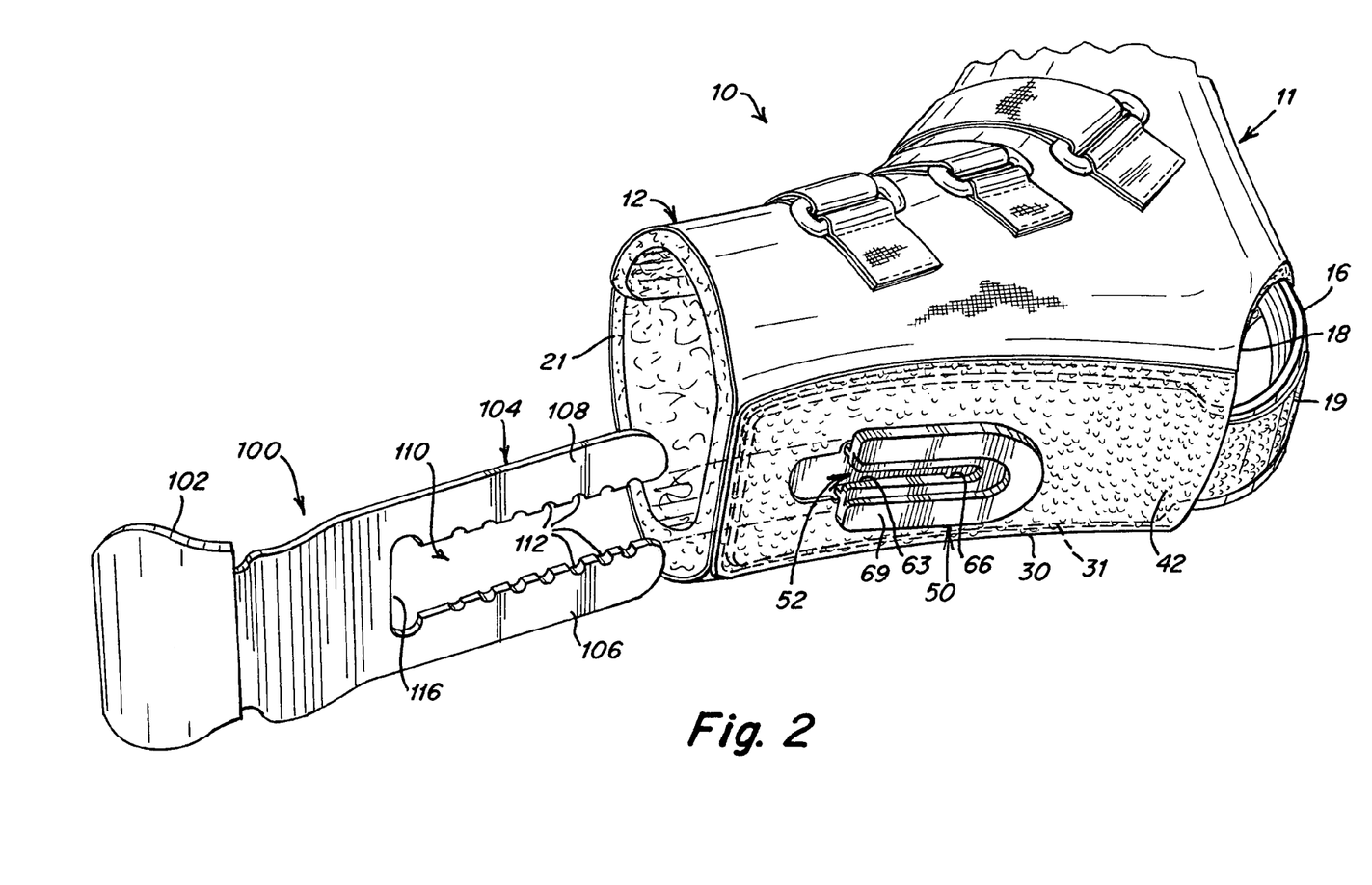
FIG. 2 is an exploded bottom perspective view of the toe plate and attachment device of the orthotic of this invention.

In the embodiment shown herein, toe plate 100 includes a toe pad 102 and engagement portion 104, and, in one embodiment, an elbow 114 between toe pad 102 and engagement portion 104. In one embodiment, as shown in FIGS. 1 and 2, engagement portion 104 includes at least one arm and preferably two generally parallel arms 106 and 108 separated by a slot 110 having a closed end 116. Arms 106 and 108 are configured to be inserted into bracket 50. As shown in FIGS. 6-8B, wall 69, which typically is generally parallel to surface 59, includes upstanding portions 68. Bracket 50 also includes outer walls 57, which are typically oriented generally perpendicularly of surface 59. Slot 110 between arms 106 and 108 is configured, typically, to surround bracket 50 so that arms 106 and 108 embrace bracket 50 along outer walls 57 and are captured between upstanding portions 68 of wall 69 and surface 59. Arms 106 and 108 are typically sufficiently flexible that they may flex outwardly in the plane of engagement portion 104 away from slot 110 and bracket 50 as toe plate 100 is slid over bracket 50. Toe plate 100 is vertically separated from sole plate 70 on bracket 50 with respect to surface 59 and the plane of the upper surface of sole plate 70, so that toe plate 100 can be inserted and removed independently of sole plate 70, and so that sole plate 70 can be removed and inserted independently of toe plate 100.

Figure 6:
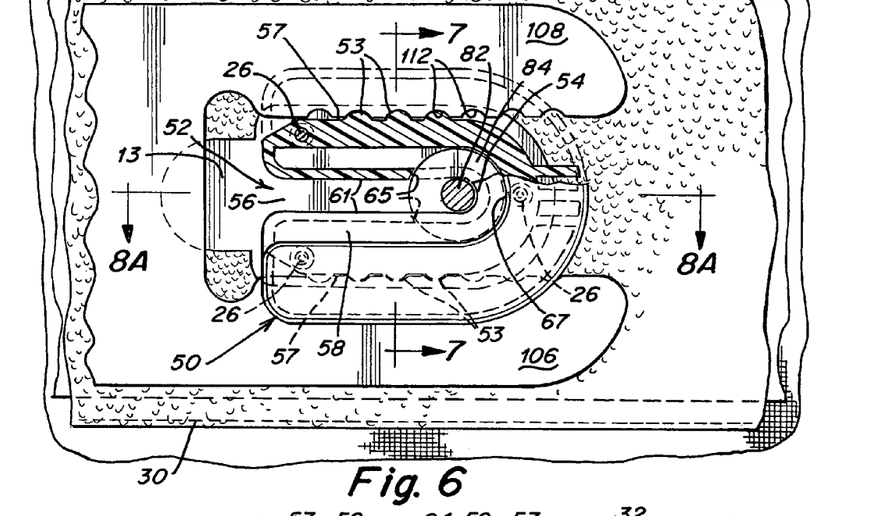
FIG. 6 is a partially broken away bottom, cross-sectional view of the attachment device taken along the line 6-6 of FIG. 5.

In another embodiment of this aspect, as shown in FIG. 6, ribs 53 may be provided along the outer surface of walls 57. In addition, recesses 112 may be provided along the inner edges of arms 106 and 108 which are configured to face and mate with ribs 53. In this way, as arms 106 and 108 are slid over walls 57, recesses 112 engage ribs 53 to retain toe plate 100 in place.

Toe plate 100 typically is formed of a somewhat flexible, resilient material, such as a plastic material, to permit the desired outward flexing of arms 106 and 108 and inward bias force on arms 106 and 108 toward one another that causes arms 106 and 108 to return to their normal, spaced condition. In addition, typically, but not necessarily, toe plate 100 provides a resilient, upward force on toe pad 102 to provide the desired support for the toes and to urge the toes into the desired orientation with respect to the foot.

As shown in FIG. 4, elbow 114 may serve as a contact point for toe plate 100 with respect to underlying surface 35 upon which a person would walk. Also, elbow 114 may provide an upward tilt to toe pad 102, so that the person's toes are lifted away from the walking surface and out of contact therewith to provide adequate protection. Elbow 114 may provide toe pad 102 and thus the toes with a desired angle with respect to the foot in a normal resting position.

In use, toe plate 100 is aligned with bracket 50 from the front end or the end facing end 21, so that arms 106 and 108 embrace bracket 50. As shown in FIG. 7, arms 106 and 108 are positioned between upstanding portions 68 and surface 59. Regardless of whether or not sole plate 70 is in position on bracket 50, the user pushes toe plate 100 laterally from toe pad 102 in a direction toward heel 18. Arms 106 and 108 flex outwardly away from bracket 50 as recesses 112 ride over ribs 53 on bracket 50. Typically, although not necessarily, toe plate 100 is advanced until end 116 of slot 112 abuts bracket 50. Ribs 53 tend to nest in correspondingly formed recesses 112, as shown in FIG. 6. The position of toe plate 100 is adjustable by simply pushing toe plate 100 laterally toward or away from heel 18 until toe pad 102 extends the desired distance from foot portion 12. Upstanding portions 68 and surface 59 limit flexing of toe pad 100 in a direction toward and away from foot portion 12 to provide the desired support and protection for the toes of a user. When it is desired to remove toe plate 100, one simply grabs toe pad 102 and pulls toe plate 100 away from foot portion 12 in a direction generally parallel to arms 106 and 108 until arms 106 and 108 are completely removed from bracket 50. Arms 106 and 108 again flex outwardly as recesses 112 slide over ribs 53.

As shown in FIG. 4, when toe plate 100 is inserted onto bracket 50, wall 69 of bracket 50 is spaced an even greater amount from a walking surface 35 than when toe plate 100 is not present, providing even more stability for a person who decides to walk using orthotic 10 without attaching sole plate 70. Moreover, the width of toe plate 100 and elbow 114 also provides a stable surface. Even without toe plate 100, as shown in FIG. 9, when end 21 contacts the underlying walking surface 35, bracket 50 is spaced from surface 35, so that between end 21 and heel 18, a stable contact is provided between orthotic 10 and underlying walking surface 35 so that a user is not in danger of twisting his or her ankle, slipping or falling over. In particular, the projection 80, which in some prior art devices is disposed on the bottom surface of foot portion 12, is now found only on sole plate 70 and therefore is only in use when sole plate 70 is attached. Since sole plate 70 provides a broad stable surface when attached to orthotic 10, no instability is created by the presence of projection 80.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A foot orthotic comprising:
   a boot, the boot comprising a toe portion comprising a forward end, a recessed arch portion and a heel;
   a sole plate removably mountable on said boot, said sole plate comprising a textured surface on a first side for engagement with a walking surface, and an upstanding projection disposed on a second side opposite of said first side;
   a bracket disposed on said boot, said bracket comprising a slot for receiving said projection on said sole plate, said bracket comprising a lower wall spaced from said boot and structured to face said sole plate, said lower wall of said bracket being spaced from a line connecting the forward end of said toe portion of said boot and said heel of said boot and on a side of said line facing said arch portion; and
   mating portions of a hook and loop fastener disposed on opposed, confronting surfaces of said boot and said sole plate.

2. The foot orthotic of claim 1 wherein said projection comprises an enlarged head disposed on an end thereof spaced from said sole plate, and wherein said bracket comprises a recess for nesting of said enlarged head.

3. The foot orthotic of claim 1 wherein said bracket comprises a slot surrounded by upstanding walls, and wherein said projection on said sole plate comprises an enlarged head spaced from said second side of said sole plate, said enlarged head being structured to ride along said upstanding walls of said bracket as said projection passes through said slot of said bracket.

4. The foot orthotic of claim 1 wherein said bracket is disposed in said recessed arch portion of said boot.

5. A foot orthotic comprising:
   a boot, the boot comprising a toe portion comprising a forward end, a recessed arch portion and a heel;
   a sole plate removably mountable on said boot, said sole plate comprising a textured surface on a first side for engagement with a walking surface, and an upstanding projection disposed on a second side opposite of said firsts side;
   a bracket disposed on said boot, said bracket comprising a slot for receiving said projection on said sole plate, said bracket comprising a lower wall spaced from said boot and structured to face said sole plate, said lower wall of said bracket being spaced from a line connecting the forward end of said toe portion of said boot and said heel of said boot and on a side of said line facing said arch portion; and a toe plate mountable on said bracket independently of said sole plate.

6. The foot orthotic of claim 5 wherein said toe plate comprises:
   a toe pad for supporting toes; and
   at least one arm insertable into said bracket at a location spaced from said sole plate for retention of said toe plate on said bracket.

7. The foot orthotic of claim 6 wherein said toe plate comprises two generally parallel arms forming a slot therebetween for embracing a portion of said bracket.

8. The foot orthotic of claim 7 further comprising mating ribs and ridges disposed on opposed, interlocking surfaces of said bracket and said arms of said toe plate.

9. In combination:
   a boot having a generally L-shaped configuration and comprising a toe portion, a heel, a concave arch portion and a leg portion;
   a sole plate removably attached to said boot and extending generally from the heel to the toe portion of the boot, said sole plate comprising an upstanding projection disposed on an upper surface thereof facing said boot;
   a bracket disposed in said concave arch portion of said boot, said bracket receiving an enlarged upper end of said projection; and
   a toe plate connected to said bracket independently of said sole plate.

* * * * *